(12) United States Patent
Pyo

(10) Patent No.: US 6,761,447 B1
(45) Date of Patent: Jul. 13, 2004

(54) CUSTOM FRAME FOR EYEGLASS LENSES AND INSTRUMENTS

(76) Inventor: Han Seung Pyo, 12393 E. Cornell Ave., Aurora, CO (US) 80014

(\*) Notice: Subject to any disclaimer, the term of this patent is extended or adjusted under 35 U.S.C. 154(b) by 0 days.

(21) Appl. No.: 10/453,816

(22) Filed: Jun. 3, 2003

Related U.S. Application Data

(60) Provisional application No. 60/385,459, filed on Jun. 4, 2002.

(51) Int. Cl.⁷ .................................................. G02C 1/00
(52) U.S. Cl. ........................... 351/41; 351/156; 351/158
(58) Field of Search .............................. 351/41, 83, 111, 351/154, 156, 158; 359/409

(56) References Cited

U.S. PATENT DOCUMENTS

| | | |
|---|---|---|
| 2,003,379 A | 6/1935 | Malcom |
| 3,006,247 A | 10/1961 | Davis |
| 3,308,816 A | 3/1967 | Franklin |
| 3,354,884 A * | 11/1967 | Rudo .......................... 604/303 |
| 3,507,493 A * | 4/1970 | Robins .......................... 482/11 |
| 3,691,565 A | 9/1972 | Galonek |
| 3,952,331 A | 4/1976 | Melville |
| 4,122,847 A * | 10/1978 | Craig .......................... 128/858 |
| 4,141,086 A * | 2/1979 | Jackson .......................... 2/436 |
| 4,157,090 A | 6/1979 | Phillips |
| 4,395,731 A | 7/1983 | Schoolman |
| 4,616,257 A | 10/1986 | Kloots |
| 4,621,378 A | 11/1986 | Hatchman |
| 4,626,378 A | 12/1986 | Berger et al. |
| 4,674,136 A | 6/1987 | Ladewig |
| 4,872,217 A * | 10/1989 | Kitayama .......................... 2/15 |
| 5,341,513 A | 8/1994 | Klein et al. |
| 5,343,258 A | 8/1994 | Lachman |
| 5,973,728 A | 10/1999 | Levitan |
| 6,135,593 A * | 10/2000 | Moyse .......................... 351/41 |
| 6,441,978 B1 | 8/2002 | Kobayashi |
| 6,641,264 B1 * | 11/2003 | Schwebel .......................... 351/62 |
| 2002/0005931 A1 * | 1/2002 | Chen-Lieh .......................... 351/43 |
| 2002/0029399 A1 | 3/2002 | Hill |

\* cited by examiner

*Primary Examiner*—Huy Mai
(74) *Attorney, Agent, or Firm*—Henry L. Smith, Jr.

(57) ABSTRACT

A support or frame which holds eyeglass prescription lenses as well as optical loupes, microscopes, lights, and similar instruments used by doctors, dentists, jewelers, or sportsman. The frame is custom fitted to the facial features of the user and throughout has large surfaces which contact many facial features of the user including the forehead, eyebrows, nose ridge, and cheeks. The large surface contact areas and an adjustable headband system enable the user to comfortably wear the device for extended periods of time despite the weight of the lights, loupes, etc. A special frame for prescription lenses is also provided, as well as methods for manufacturing the device.

28 Claims, 10 Drawing Sheets

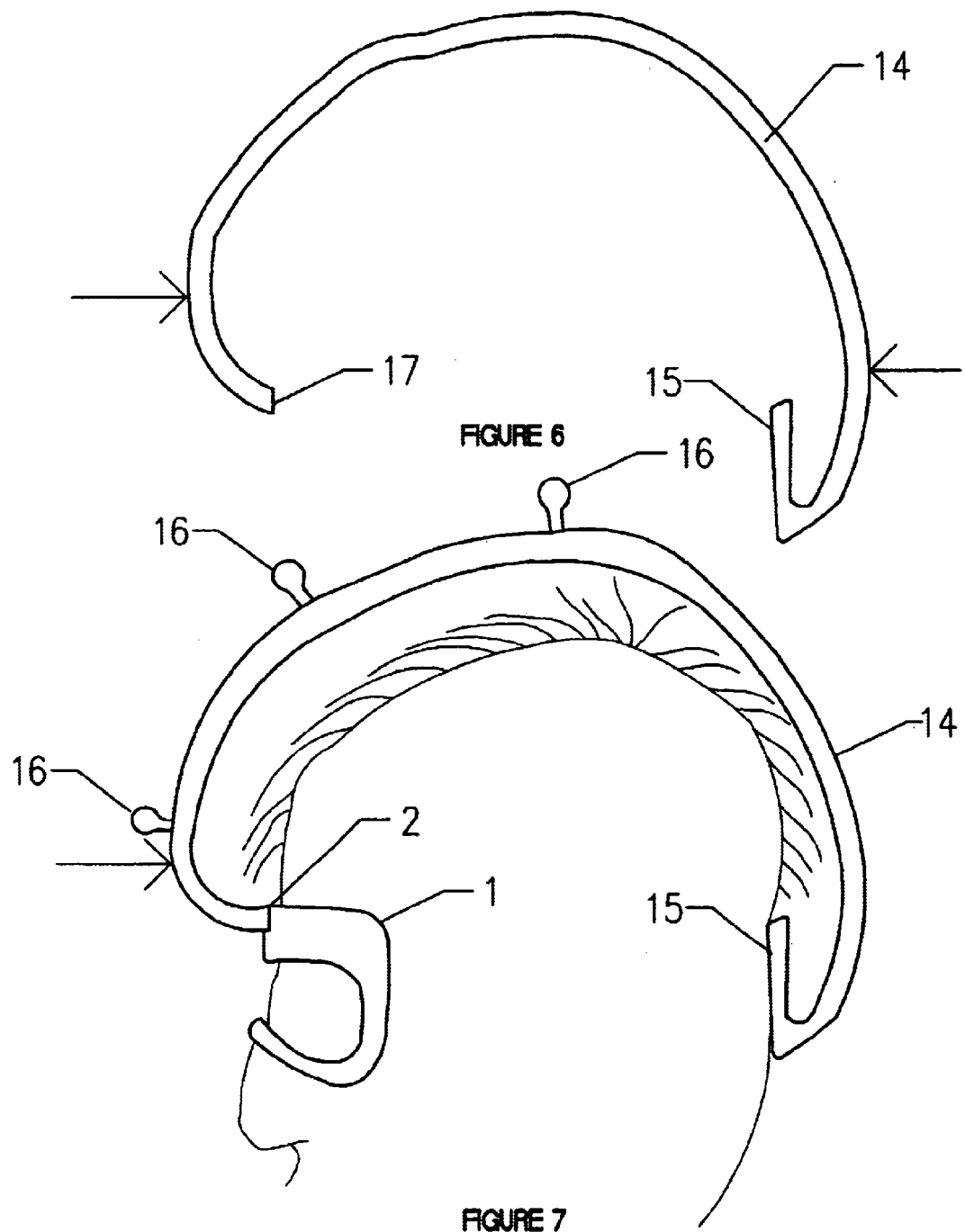

CUSTOM FRAME FOR EYEGLASS LENSES AND INSTRUMENTS

CROSS REFERENCE TO RELATED APPLICATIONS

This application claims the priority filing data of U.S. provisional application No. 60/385,459 filed Jun. 4, 2002.

BACKGROUND-FIELD OF THE INVENTION

The field of the invention is a group of frames for supporting eyeglass prescription lenses (or plain glass for eye protection) and lights, optical loupes, cameras, and small microscopes near the eyes of users such as doctors, dentists, and other professionals during medical or dental procedures, and such as jewelers and others who must work with very small parts or details. The device could also be used with lights by persons engaged in various sports including cave exploring and swimming.

BACKGROUND-DESCRIPTION OF PRIOR ART

Representative of prior art is U.S. Pat. 4,395,731, Jul. 26, 1983 to Schoolman. This patent discloses a kind of goggles to be worn on the head of a physician or dentist which includes devices in front of the eyes to provide a magnified view for manual manipulations of a patient especially those during surgery.

SUMMARY OF INVENTION

The invention is a frame for supporting prescription eyeglass lenses (or plain glass for eye protection) near the eye of the user, and in addition various other devices such as lights, magnifying glasses, microscopes, etc. for use by dentists and physicians while performing medical procedures, or for use with lights by those engaged in sporting activities including cave exploring and swimming. The frame on which such lenses and devices are mounted is specially designed to accommodate a wide range of different facial features of various individuals, especially those from different ethnic groups, such as differences in the size, shape, and placement of the forehead, eyebrows, nose bridge, and cheekbones. The invention enables individuals to wear the invention, including heavier attachments such as lights and microscopes, for long periods of time with great comfort because: (a) the shape and contact areas of the frame supporting the lenses and devices is custom-designed for the facial features of the individual who will wear it, and (b) the frame features a large area of contact with various facial features thus reducing uncomfortable pressure on the face of the user and thus distributing the weight of the frame and attached devices over a broad area of the user's face. This enables the user to wear the frame comfortably for extended periods of time. Another aspect of the invention is the process for a custom fitting of the frame to the particular facial structure of the wearer. This can be accomplished by at least three processes. First, a facial model of substantially all the face of the user can be made by conventional plaster model techniques, and this model can serve as the basis for shaping and manufacturing the frame of the device to fit the facial features of the user and to provide extended areas of contact with the user's facial features thus avoiding pressure points. In this method, a chemical hardening plastic such as methyl methacrylate available from Dentsply International, P. O. Box 872, York, Pa. 17405-0872, well known to those skilled in the art, is pressed against the model and then allowed to harden. Secondly, the user's face can be scanned by a laser or other device which is connected to a computer which stores the dimensions and topography of the user's face in the computer and uses that as a basis for manufacturing a custom device for the user through well-known CAD/CAM (computer aided design/computer aided manufacturing) processes. Typical equipment for such scanning and CAD/CAM design and manufacturing is available from Sirona Company, Charlotte, N.C. Thirdly, a custom frame specially shaped for the face of the user can be produced or selected by the user himself using a kit provided by the manufacturer. The kit contains flexible plastic or similar material in the general shape of a frame which can be custom shaped by the user to his own face in a manner which provides extended surface contact with the facial features of the user. Once the shaping is done, the plastic is hardened by light treatment by processes known to those skilled in the art. Such plastic curable by exposure to light is light curable acrylic resin and is available from Dentsply International, P. O. Box 872, York, Pa. 17405-0872. Alternatively, the user can be sent a set of a number of frame templates of different sizes, so that the user can choose the one with a shape most compatible with his facial features. The manufacturer is then informed which frame is the best fit, and the manufacturer then sends the user a frame, made of flexible light curable plastic, closely resembling the best template. Upon receipt of this frame, the user by finger pressure custom fits the frame to his exact facial features, and then hardens the plastic by exposure to light. In each case the frame received by the user contains the headband retaining pins. The frame is held on the head of the user by means of side arms which go over the ears like conventional eyeglasses and by a headband, and there are large contact surfaces with the facial features of the user, and a flexible headband system which engages the back of the user's head.

The invention also includes the methods of custom shaping the frame with large contact area against the particular facial features of the user. The means for retaining the frame on the user's head includes glasses-like side arm means, various headband means attached to the frame and contacting various areas of the user's head, and resilient top headband means.

OBJECTS AND ADVANTAGES

The objects of the present invention are:

1. To provide a support or frame for prescription lenses, lights, microscopes, and other similar equipment for use by doctors, dentists, and other health-care professionals in carrying out medical and dental procedures, or by jewelers or others who work with small parts or details.
2. To provide such a support for prescription lenses and lights to be worn by those engaged in sports, including cave exploring and swimming.
3. To provide a support which is capable of securely holding the lenses, lights, microscopes etc. in place on the head of the user.
4. To provide a support which is capable of being worn comfortably for extended periods of time despite the substantial weight of the attachments.
5. To provide a support which is comfortable because of its large area of contact with several facial features including the forehead, the eyebrow area, the nose bridge, and cheekbones.
6. To provide a support which is custom-designed to the individual face of the user, and which provides extended contact area with the facial features of the user thus avoiding pressure points.
7. To provide such a support which is easily custom-designed to the individual face of the user by manufacturing based on a facial mold of the user, a laser or light scan the user's face coupled with CAD/CAM design and manufacturing techniques, or by means of a kit containing a frame in flexible plastic from which the user can form in perfect conformity with his particular facial features, and with an extensive contact area with those facial features.

8. To provide a support which is easily adapted in a custom manner to widely varying facial features of individuals of different sizes and ethnic backgrounds, in a manner which accommodates different configurations and sizes of nose bridges, etc.

9. To provide a support which is held on the head by various headband configurations, so that the weight of lights or microscopes, etc. does not cause the support to be displaced on the face of the user.

10. To provide a secure and precisely positioned support for an optical loupe or microscope in front of the user's eyes, so that the instrument does not slip up or down or side to side.

DRAWING FIGURES

FIG. 6 shows the top headband prior to expanding to fit over the top of the user's head.

FIG. 7 shows the top headband attached to the frame and in position over the top of the user's head.

Figure 1:
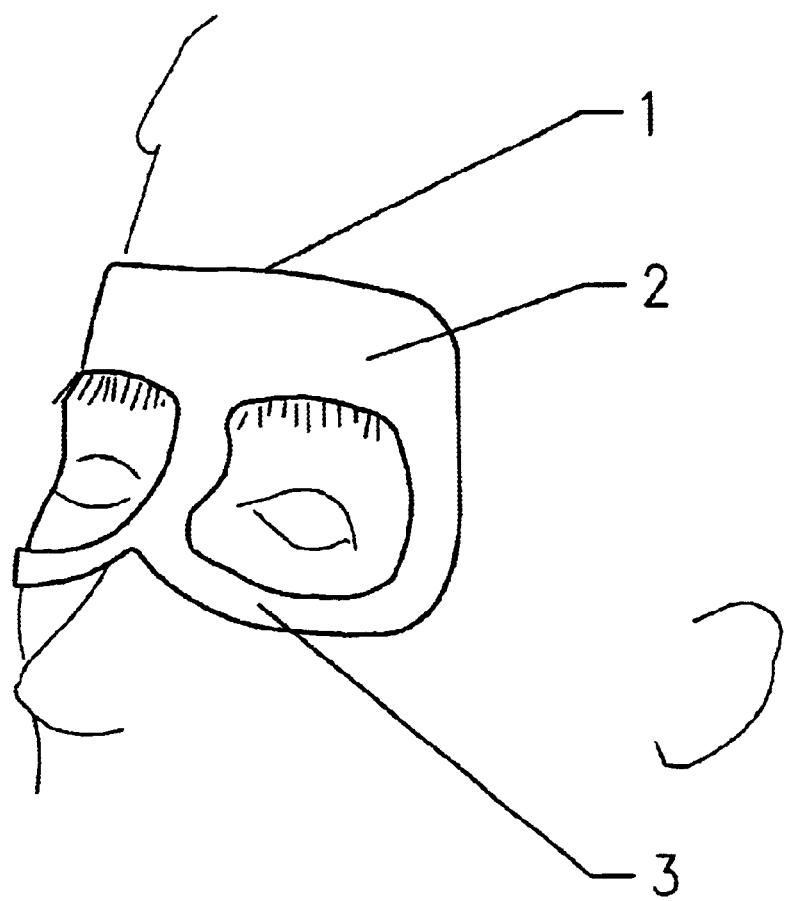
FIG. 1 shows the frame of the device with broad contact areas on the forehead, nose bridge and cheekbones.

REFERENCE NUMERALS IN DRAWINGS 1 frame
2 upper frame portion
3 lower frame portion
4 side arms
5 behind ear bone hook
6 prescription eye lens
7 light attachment
8 headband retaining pins
9 headband
10 headband retainer
12 mask holder
13 headband adjustment hole
14 top headband
15 top headband engaging surface
16 attachment knobs
17 top headband attachment area
19 close vision area
20 medium vision area
21 distance vision area
22 lens retaining notch
23 lens retainer frame
24 lens retainer point
25 lens frame groove

DETAILED DESCRIPTION OF THE DRAWINGS

Figure 2:
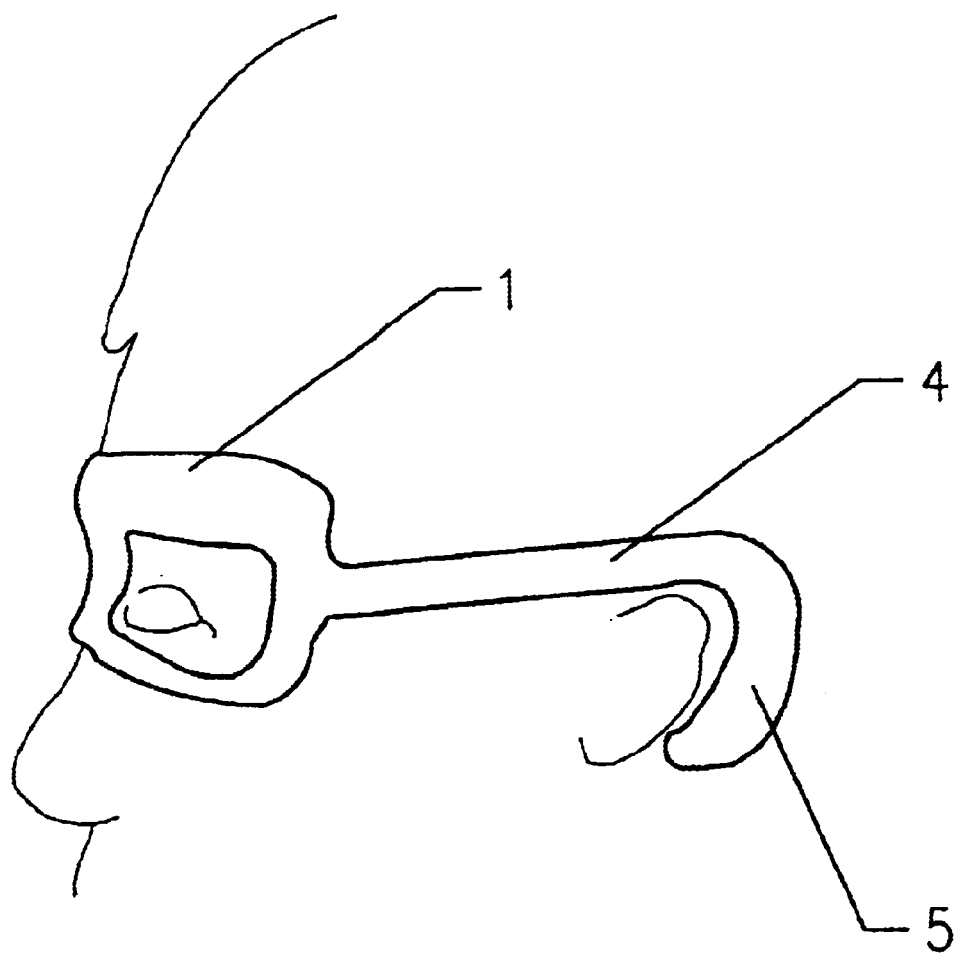
FIG. 2 shows the side arm of the frame and curved behind ear bone hook.
Figure 3:
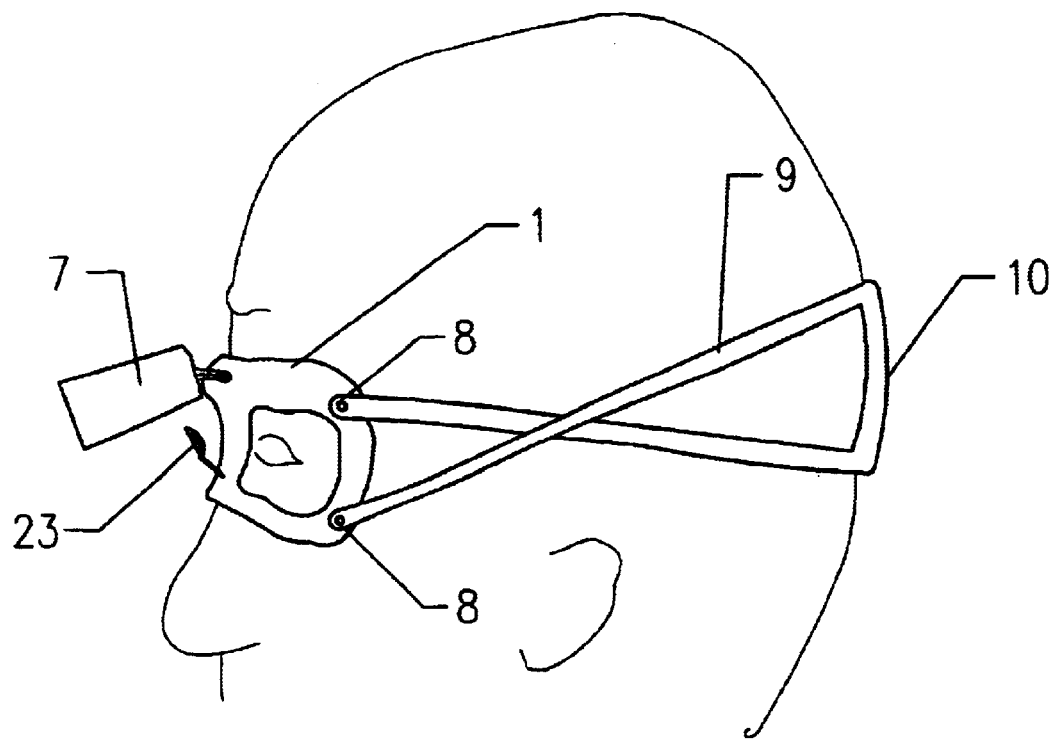
FIG. 3 shows the frame with headband instead of side arms, and a light and prescription lenses mounted on the frame.
Figure 4:
FIG. 4 shows a mask holder attached to the frame.
Figure 5:
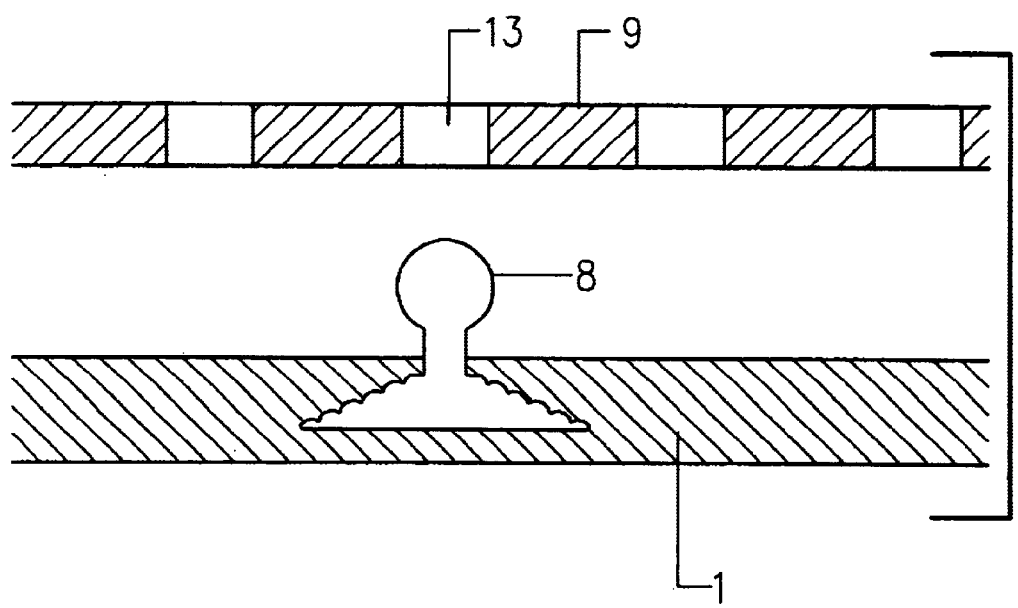
FIG. 5 is a close up cross section of the frame showing headband retaining pins embedded in it, and adapted to snap into holes in the headband.
Figure 8:
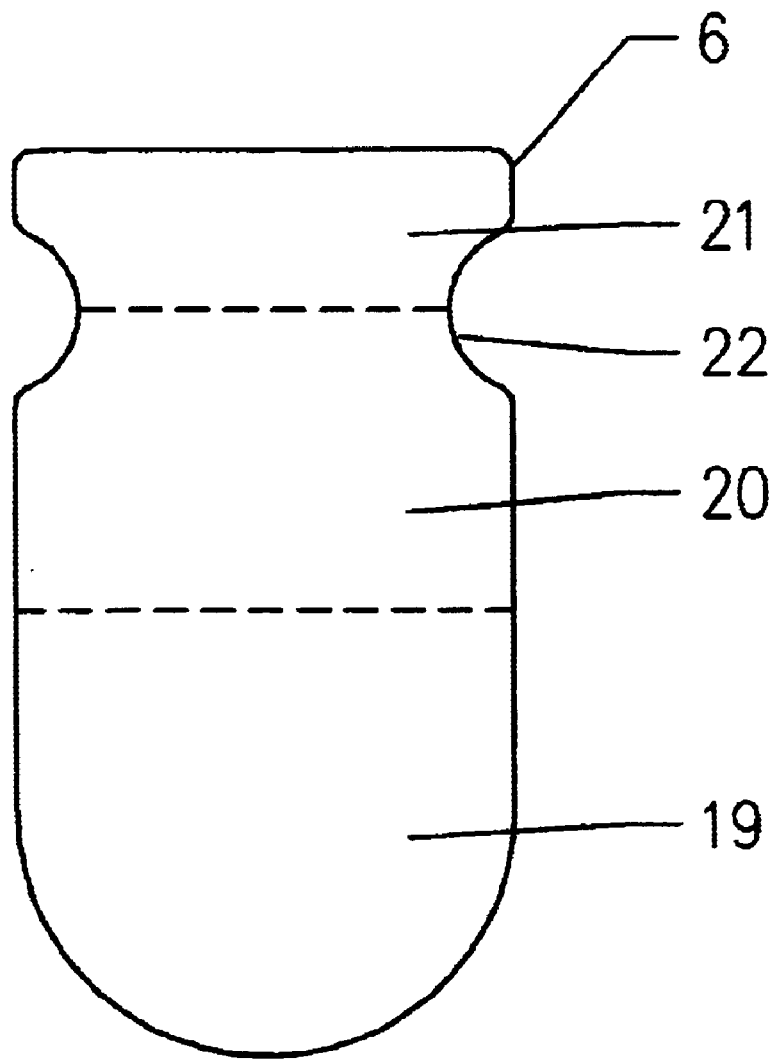
FIG. 8 shows a trifocal prescription lens with three vision areas.
Figure 9:
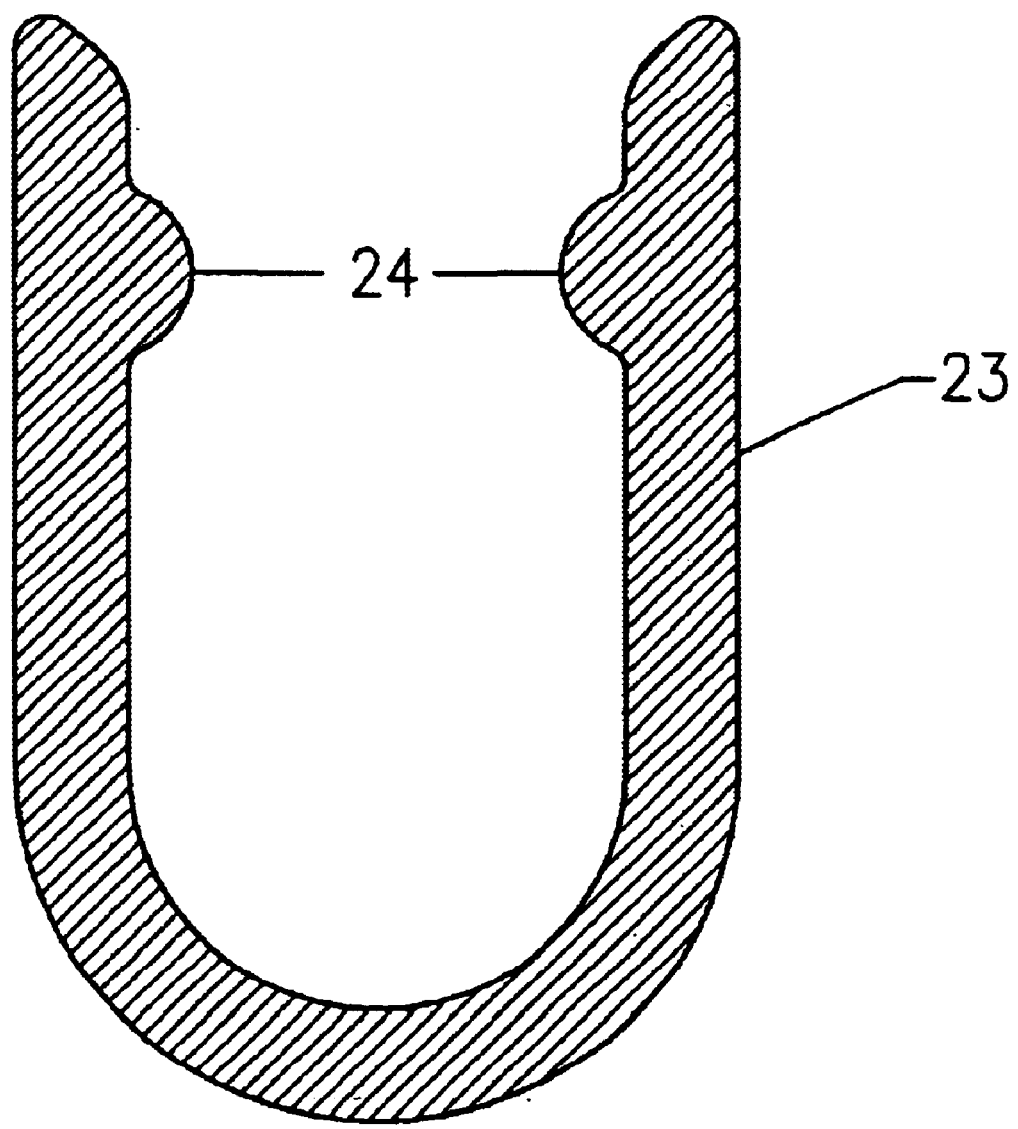
FIG. 9 shows the lens retainer frame.
Figure 10:
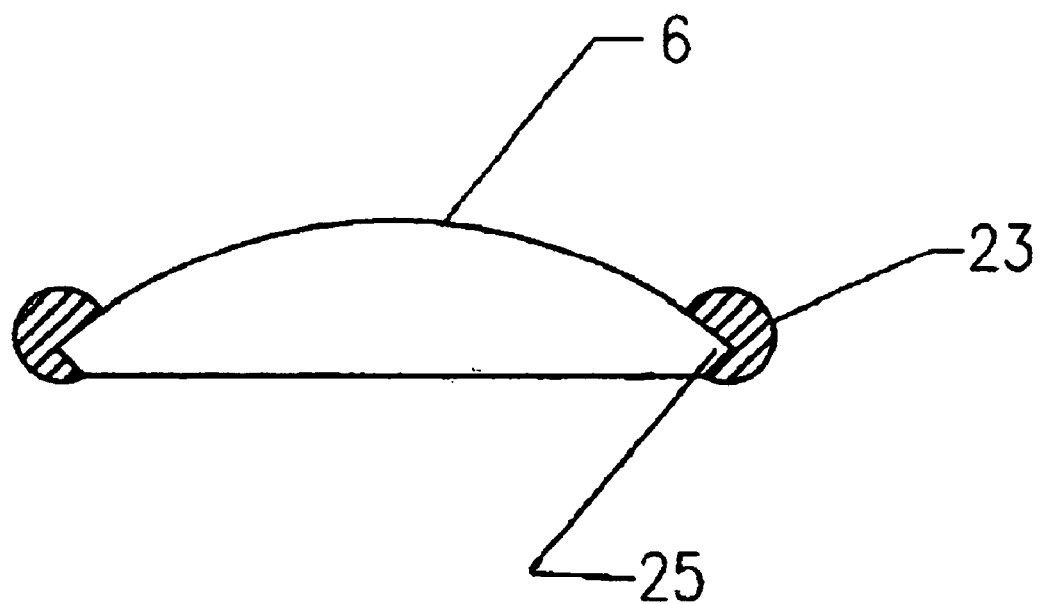
FIG. 10 shows the prescription lens in the lens retainer frame and held in the lens frame groove.
Figure 11:
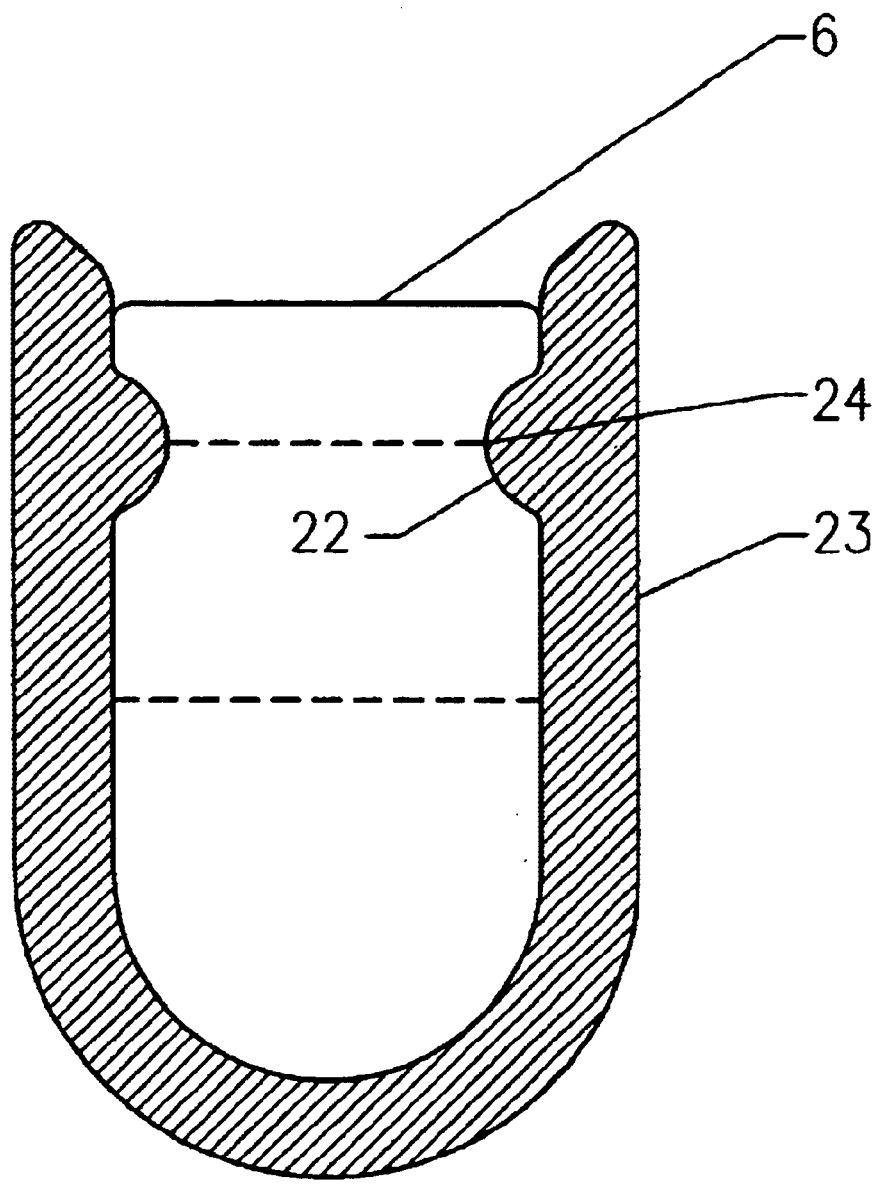
FIG. 11 shows the prescription lens in position in the lens retainer frame.

FIG. 1 shows the frame 1 on the face of the user. Upper frame portion 2 and lower frame portion 3 have large contact areas with the forehead and cheeks of the user. The nose bridge portion of the frame has a large contact area with the user's nose. FIG. 2 shows the frame 1 and one side arm 4 extending back to behind ear bone hook 5 over the user's ears and pressing against the bone over the top of the ear with a large contact area. FIG. 3 shows frame 1 held in place by side headbands 9 connected at headband retainer 10 in the back of the user's head. The headbands 9 are held to the frame 1 by various attaching means including headband retaining pins 8 having one end embedded in frame 1. Lens retainer frame 23 and light attachment 7 are shown attached to frame 1. FIG. 4 shows mask holder 12 attached to frame 1, comprising three rod-like members attached at three points on frame 1 and attached to each other under the user's chin. A sanitary mask can be attached over 12 by various means including tape, clips, elastic, and other means known to those skilled in the art. FIG. 5 is a closeup sectional view of a headband retaining pin 8 shown embedded in frame 1 and capable of being snapped through headband adjustment hole 13 in headband 9. FIG. 6 shows another possible headband, the top headband 14, in its un-stretched position. FIG. 7 shows the top headband 14 in position on the user's head. The side headbands are not shown in the FIG. 8 shows a section of a trifocal prescription lens 6 with rounded lower corners and a lens retaining notch 22 in each side. FIG. 9 is a front view which shows the lens retainer frame 23 which holds the prescription lens 6, and lens retainer point 24. FIG. 10 is a top cross sectional view of prescription lens 6 held in position in lens retainer frame 23 by means of a lens frame groove 25 inside the frame. FIG. 11 shows the lens 6 held in position in lens retainer frame 23 by means of the engagement of the lens retainer point 24 positioned in the lens retaining notch 22. In this way lenses for such frames may be made in a standard shape and size so that the user can insert the lenses in lens retainer frame 23 by himself without visiting an optician.

DESCRIPTION-PREFERRED EMBODIMENT

In the preferred embodiment of the invention, the frame 1 for prescription eyeglass lenses 6, optical loupes, microscopes, and lights 7 etc. is formed by either a laser scan of the face coupled with CAD/CAM design and manufacturing, or the frame is formed by the user based on a kit of flexible plastic in the general shape of eyeglass frame, which is then hardened by light treatment. Typically prescription eyeglass lenses are cut down to pieces about 2 cm by 2.5 cm with curved bottom corners, and then put into a plastic lens retainer frame 23 typically made of acrylic resin or material similar to the main frame. The prescription eyeglass lenses 6 in their frames 23 are then glued to the plastic of the frame 1 and held in place by acrylic glue, so that most examples of the frame of the invention include prescription lenses for the user. The prescription lenses must be properly aligned in the line of vision of the user, and usually angled downward depending on the typical position of the user and the work he is doing. For example, since dentists typically sit near the patient, and surgeons typically stand over the patient, the strength of the prescription lenses and their downward angle in the frame would be adjusted accordingly by methods well known to those skilled in the art. The upper portion 2 of the frame near the forehead or eyebrows of the user is adapted to support optical loupes, microscopes, lights etc. by various methods known to those skilled in the art including attaching such devices to the upper frame 2, or side arms 4 going over the ears, by gluing, clamps, screws, pins, or other simple mechanical means known into those skilled in the art. The preferred embodiment of the invention includes large surface contact areas between the frame 1 and several areas of the user's face including forehead, eyebrows, nose bridge, and cheek bones, thus spreading pressure against the skin due to the weight of the attached devices over a large area of skin surface thus reducing pressure points and increasing comfort and allowing the user to wear the frame for extended periods of time. To create substantial contact area with the skin and facial features of the user, the flat surfaces of the frame 1 in contact with the user's facial features would typically be about 1–7 cm in width and about 3 mm thick, formed from plastic or metal. In the preferred embodiment, the side arms 4 of the frame go over the ears of the user like conventional eyeglasses but also press against the bone behind the ear with a broad area of contact. The upper frame portion 2 is placed on the eyebrow and the forehead, and the middle portion of the frame is placed on the bridge of the nose, by means of a large contact area. The lateral part of the frame is placed about 1 cm from the lateral corner of the eye. The lower frame portion 3 is placed on the cheekbones. For the heavier loupes or lights or camera, a headband 9 also extends around the lower back of the head to prevent these heavier objects from causing the frame to be displaced on the face. The preferred embodiment would also involve a flexible headband 9 of various possible configurations which could go over the back and side of the user's head, and which is attached to the frame 1 in an adjustable manner to allow for differences in head shapes and sizes. In the preferred embodiment of the headband, one or more bands are attached to the frame 1 through adjustable attachment means. An example of such attachment means include Velcro (hook and loop) pairs, mating snap buttons, headband retaining pins 8 in the frame 1 which are capable of penetrating one of several headband adjustment holes 13 in the headbands 9, thus allowing for variations in head shape and size and variations in snugness of the bands against the user's head. In one embodiment, two crossed headbands 9 as shown in FIG. 3 cross just above the user's ear and provide extra stability for the band arrangement by touching the head above the user's ear. Another kind of headband is shown in FIGS. 6 and 7. The top headband 14 could be made of injection molded nylon or similar material. FIG. 6 shows top headband 14 in its un-stretched position. The user stretches the headband farther open with his hands as he puts it on his head. Top headband attachment area 17 is positioned in a depression (not shown) at the center of the upper frame portion 2. The resilience of the top headband 14 keeps it in place on the head by force exerted against the center of the upper frame portion 2, and against the back of the user's head at top headband engaging surface 15. The resilience of the headband keeps it in position in the depression in center of the upper frame portion 2. The top headband engaging surface 15 is shown pressing against the back of the user's head. The top headband attachment area 17 presses against the frame 1 and helps to keep it in place on the user's face. Alternatively, the top headband attachment area 17 can be more securely attached to the center of the upper frame portion 2 by gluing it to the frame 1 or by various other simple mechanical attachments means well known to those skilled in the art. The top headband 14 can also be fitted with attachment knobs 16, for attaching a cable from a light mounted on frame 1, or a surgical cap or other accessories. The advantage of the top headband 14 is that it does not press against or disturb the user's hair. The top headband 14 is typically 2–5 mm thick and is in the shape of an arced flat strip typically 1 to 2 cm wide. If there is not enough tension from the nylon top headband, a headband made of stainless steel could be used, or a small stainless steel headband of the same shape and size of the nylon top headband could be attached along most of the outside circumference of the nylon top headband by attaching it to attachment knobs 16, thus giving it more stiffness. A resilient side headband similar to the resilient top headband could also be used—a resilient side headband means connected to the upper portion of the frame and designed to extend over the side of a user's head and end at the lower back area of a user's head, where the resilient side headband means is shaped, sized, and tensioned to retain stable contact with the back of a user's head at one end of the headband; and so as to retain the frame around the eyes of a user at the other end of the headband, due to the tensioning of the headband.

Prescription lenses are attached to frame 1 by the following method. FIG. 8 shows a trifocal lens 6 which has been cut from a lens piece approximately 2 cm by 2.5 cm. The lower left and right edges, usually in the close vision area 19, are rounded. Near the top of the lens, a lens retaining notch 22 is cut into the two upper opposite sides of the lens. FIG. 9 shows the lens retainer frame 23, typically made of somewhat flexible plastic so that the u-shape can be stretched open somewhat. The thickness of the frame 23 is about 3 mm. The two opposite edges of the lens 6 are slipped down into the lens retainer frame 23 and are held in place in the lens frame groove 25 which is cut into the entire inside u-shaped surface of lens retainer frame 23. As the lens slides down in the groove 25, the frame 23 is forced open somewhat as the lens retainer points 24 press against the sides of the lens 6. When the bottom of the lens reaches the bottom of the lens retainer frame 23, the lens retainer points 24 snap into the lens retaining notches 22, and the lens is held securely in place in groove 25 by the lens retainer points 24. The lenses 6 can be removed from the lens retainer frame 23 by stretching open the upper portion of the u-shape of the frame, thus disengaging the lens retainer points 24 from lens retaining notches 22.

OPERATION OF THE INVENTION

In the operation of the invention, the facial features of the user are determined by a custom process including: full face plaster mold and chemical hardening plastic, a scan of the face by a CAD/CAM scanning and computer system, or using a flexible plastic frame from a kit which the user shapes to his own face by finger pressure, and then hardens by light. During this process of shaping the plastic frame to the user's face, care is taken to be sure that the frame is shaped so that there is extensive contact area between frame and the skin of the user including the forehead, eyebrows, nose bridge, and cheeks. Once the frame is manufactured, it is fitted with a side or top headband. By means of adjustable attachment means, the headband is capable of different degrees of snugness against the user's head. The lens retainer frame 23 is attached to the main frame 1 as follows. The frames 23 are temporarily secured to the loupe eyepieces on the ends nearest the eye. The loupe is then mounted to the horizontal upper frame portion 2 by gluing, clamping or other attaching means. After this assembly the loupe can be pivoted down or around into the user's line of sight as desired, and then the frame 23, now properly positioned and angled with respect to the frame 1, is glued to the lower frame portion 3, and then the frame 23 is released from the loupe, so that the loupe may again moved out of the user's line of sight.

TESTS

The Applicant has performed tests of these procedures and structures which produced a frame having a large contact area with his facial features and which enabled him to wear the frame for very extended periods of time very comfortably without pressure points against his facial features. Prescription eye lenses were also added to the frame, and an optical loupe or small binocular microscope was attached to the upper horizontal portion of the frame 2 thus allowing them to be pivoted into the user's line of sight. The test version of the frame involved headband retaining pins 8 with round heads attached to the frame 1 which could engage headband adjustment holes 13 in headbands 9 which provided greater stability of the frame on the head of the user The test version of the frame was produced by molding flexible plastic against the Applicant's face by finger pressure and hardening the plastic with light. This produced a very satisfactory and comfortable frame which the Applicant has used for extended periods in his work as a dentist, and which includes his eyeglass prescription lenses and an optical loop or microscope which he uses in his work.

ADDITIONAL EMBODIMENTS

In an additional embodiment of the invention, a mask holder 12 may be attached to the lower frame portion 3 beneath the eyes in a manner so that the mask holder extends downwardly over the nose and mouth of the user, thus protecting the user from fluid splashes or germs from the patient. Surgical or sanitary masks of various types can be attached to the mask holder by methods well known to those skilled in the art. The mask holder and mask prevent the prescription lenses and other optical instruments from being fogged by the user's breath. The mask holder can be designed to hold the mask in a position so that the mask does not touch the user's mouth for greater comfort and better breathing and speaking.

CONCLUSIONS, RAMIFICATIONS AND SCOPE

A number of changes are possible to the structures and methods described above, while still remaining within the scope and spirit of the invention. Many kinds of plastic or other materials may be used for parts of the invention.

The specifics about the form of the invention described in this application are not intended to be limiting in scope. The scope of the invention is to be determined by the claims, and their legal equivalents, not the examples given above.

I claim:

1. A support for prescription lenses, microscopes, optical loupes, lights, and other accessories for detailed work by a user, comprising an eyeglasses-like frame for positioning around the eyes of a user, wherein the area of contact between the frame and the face of a user is large, so as to avoid pressure points on the face of a user, and wherein the area of contact between the frame and the face of a user includes most of the nose bridge, the forehead, eyebrows, and the cheekbone area of a user's face.

2. The support of claim 1, further comprising a frame retaining means comprising one or more of the means selected from the group consisting of:

(a) eyeglasses-like sidearm means attached to the side portion of the frame and designed to hook over the top and back of a user's ear, (b) one or more headband means connected to the side of the frame and designed to extend around the sides and back of a user's head, (c) a resilient top headband means connected to the upper portion of the frame and designed to extend over the top of a user's head and end at the lower back area of a user's head, wherein the resilient top headband means is shaped, sized, and tensioned to retain stable contact with the back of a user's head at one end of the top headband, and so as to retain the frame around the eyes of a user at the other end of the top headband, due to the tensioning of the top headband, (d) a resilient side headband means connected to the upper portion of the frame and designed to extend over the side of a user's head and end at the lower back area of a user's head, wherein the resilient side headband means is shaped, sized, and tensioned to retain stable contact with the back of a user's head at one end of the headband, and so as to retain the frame around the eyes of a user at the other end of the headband, due to the tensioning of the headband.

3. The device of claim 2, further comprising prescription lenses attached to the frame and positioned in the line of vision of a user.

4. The device of claim 3 made by a process comprising selection by a user of one of several frame templates best corresponding to his facial features, and a manufacturer's providing to a user a flexible light hardenable plastic frame the shape of which corresponds to the shape of the selected template and is adapted to fit a user's face with large contact areas including the forehead, nose bridge, and cheekbone areas, and a user's final shaping of the flexible plastic of the frame to his face, and then hardening the plastic frame with light.

5. The device of claim 3 made by a process comprising scanning a user's face with a scanner connected to a computer and then manufacturing the frame to conform to a user's exact facial features by CAD/CAM design and manufacturing process.

6. The device of claim 3, wherein the prescription lenses are attached to the frame by gluing or cementing to the frame, lens retainer frames positioned around each lens, wherein each lens has one or more lens retaining notches on the side edges of the lens, wherein the lens retainer frame is u-shaped and comprises a groove formed along substantially the entire inside surface of the u-shaped frame, and one or more lens retainer points positioned on the inside vertical surface of the u-shaped frame, and positioned to engage one or more lens retaining notches in the lens when the lens is inserted into the groove in the u-shaped lens retainer frame.

7. The device of claim 2, farther comprising two or more headband retaining pins with one end of the pins embedded in the frame and a rounded end of the pins projecting outwardly from the frame, wherein the pins are positioned and adapted to snap into one of several headband adjustment holes in the headband, whereby the snugness of a headband and frame combination can be adjusted.

8. The device of claim 7 made by a process comprising selection by a user of one of several frame templates best corresponding to his facial features, and a manufacturer's providing to a user a flexible light hardenable plastic frame the shape of which corresponds to the shape of the selected template and is adapted to fit a user's face with large contact areas including the forehead, nose bridge, and cheekbone areas, and a user's final shaping of the flexible plastic of the frame to his face, and then hardening the plastic frame with light.

9. The device of claim 7 made by a process comprising scanning a user's face with a scanner connected to a computer and then manufacturing the frame to conform to a user's exact facial features by CAD/CAM design and manufacturing process.

10. The device of claim 2, further comprising a mask holder attached to the frame, wherein said mask holder comprises a vertical rod-like member attached to the bottom portion of the frame at a point generally over the nose bridge of a user, a second rod-like member attached to the right lateral bottom portion of the frame at a point generally over the right cheek of a user, a third rod-like member attached to the left lateral bottom portion of the frame at a point generally over the left cheek of a user, and wherein the three vertical members are joined at a point generally below the chin of a user, and wherein the members are shaped and positioned to avoid contact with the skin of the user.

11. The device of claim 2, wherein the frame is custom manufactured for the particular face of a user by a process comprising making a model of the face of a user from plaster or similar shapeable material, producing the frame to conform to a user's face and to provide large contact area with a user's face including forehead, nose bridge and cheekbone areas, wherein the production of the frame comprises shaping a mixture of chemical hardening plastic to a model of a user's face, and then allowing the frame to harden.

12. The device of claim 2 made by a process comprising selection by a user of one of several frame templates best corresponding to his facial features, and a manufacturer's providing to a user a flexible light hardenable plastic frame the shape of which corresponds to the shape of the selected template and is adapted to fit a user's face with large contact areas including the forehead, nose bridge, and cheekbone areas, and a user's final shaping of the flexible plastic of the frame to his face, and then hardening the plastic frame with light.

13. The device of claim 2 made by a process comprising scanning a user's face with a scanner connected to a computer and then manufacturing the frame to conform to a user's exact facial features by CAD/CAM design and manufacturing process.

14. A process for making the frame of claim 2, comprising shaping the frame, made of flexible light hardenable plastic, so as to have large contact areas with a user's face, including the forehead, the nose bridge, and the cheekbone area, by pressing a light hardenable flexible plastic frame against a user's face, and then hardening the frame by light.

15. The product made by the process of claim 14.

16. The device of claim 1, further comprising prescription lenses attached to the frame and positioned in the line of vision of a user.

17. The device of claim 16 made by a process comprising selection by a user of one of several frame templates best corresponding to his facial features, and a manufacturer's providing to a user a flexible light hardenable plastic frame the shape of which corresponds to the shape of the selected template and is adapted to fit a user's face with large contact areas including the forehead, nose bridge, and cheekbone areas, and a user's final shaping of the flexible plastic of the frame to his face, and then hardening the plastic frame with light.

18. The device of claim 16 made by a process comprising scanning a user's face with a scanner connected to a computer and then manufacturing the frame to conform to a user's exact facial features by CAD/CAM design and manufacturing process.

19. The device of claim 16, wherein the prescription lenses are attached to the frame by gluing or cementing to the frame, lens retainer frames positioned around each lens, wherein each lens has one or more lens retaining notches on the side edges of the lens, wherein the lens retainer frame is u-shaped and comprises a groove formed along substantially the entire inside surface of the u-shaped frame, and one or more lens retainer points positioned on the inside vertical surface of the u-shaped frame, and positioned to engage one or more lens retaining notches in the lens when the lens is inserted into the groove in the u-shaped lens retainer frame.

20. The device of claim 1, further comprising two or more headband retaining pins with one end of the pins embedded in the frame and a rounded end of the pins projecting outwardly from the frame, wherein the pins are positioned and adapted to snap into one of several headband adjustment holes in a headband, whereby the snugness of the headband and frame combination can be adjusted.

21. The device of claim 20 made by a process comprising selection by a user of one of several frame templates best corresponding to his facial features, and a manufacturer's providing to a user a flexible light hardenable plastic frame the shape of which corresponds to the shape of the selected template and is adapted to fit a user's face with large contact areas including the forehead above the eyebrows, the nose bridge, and the cheekbone areas, and a user's final shaping of the flexible plastic of the frame to his face, and then hardening the plastic frame with light.

22. The device of claim 20 made by a process comprising scanning a user's face with a scanner connected to a computer and then manufacturing the frame to conform to a user's exact facial features by CAD/CAM design and manufacturing process.

23. The device of claim 1, further comprising a mask holder attached to the frame, wherein said mask holder comprises a vertical rod-like member attached to the bottom portion of the frame at a point generally over the nose bridge of a user, a second rod-like member attached to the right lateral bottom portion of the frame at a point generally over the right cheek of a user, a third rod-like member attached to the left lateral bottom portion of the frame at a point generally over the left cheek of a user, and wherein the three vertical members are joined at a point generally below the chin of a user, and wherein the members are shaped and positioned to avoid contact with the skin of the user.

24. The device of claim 1, wherein the frame is custom manufactured for the particular face of a user by a process comprising making a model of the face of a user from plaster or similar shapeable material, producing the frame to conform to a user's face and to provide large contact area with a user's face including forehead, nose bridge and cheekbone areas, wherein the production of the frame comprises shaping a mixture of chemical hardening plastic to a model of a user's face, and then allowing the frame to harden.

25. The device of claim 1 made by a process comprising selection by a user of one of several frame templates best corresponding to his facial features, and a manufacturer's providing to a user a flexible light hardenable plastic frame the shape of which corresponds to the shape of the selected template and is adapted to fit a user's face with large contact areas including the forehead, nose bridge, and cheekbone areas, and a user's final shaping of the flexible plastic of the frame to his face, and then hardening the plastic frame with light.

26. The device of claim 1 made by a process comprising scanning a user's face with a scanner connected to a computer and then manufacturing the frame to conform to a user's exact facial features by CAD/CAM design and manufacturing process.

27. A process for making the frame of claim 1, comprising shaping the frame, made of flexible light hardenable plastic, so as to have large contact areas with a user's face, including the forehead, the nose bridge, and the cheekbone area, by pressing a light hardenable flexible plastic frame against a user's face, and then hardening the frame by light.

28. The product made by the process of claim 27.

* * * * *